US011975020B2

(12) United States Patent
Bachwich

(10) Patent No.: US 11,975,020 B2
(45) Date of Patent: *May 7, 2024

(54) COLON LAVAGE SYSTEM

(71) Applicant: Dark Canyon Laboratories, LLC, Rapid City, SD (US)

(72) Inventor: Dale R. Bachwich, Rapid City, SD (US)

(73) Assignee: Dark Canyon Laboratories, LLC, Rapid City, SD (US)

( * ) Notice: Subject to any disclaimer, the term of this patent is extended or adjusted under 35 U.S.C. 154(b) by 349 days.

This patent is subject to a terminal disclaimer.

(21) Appl. No.: 17/158,583

(22) Filed: Jan. 26, 2021

(65) Prior Publication Data

US 2021/0268018 A1 Sep. 2, 2021

Related U.S. Application Data

(60) Continuation of application No. 16/786,541, filed on Feb. 10, 2020, now Pat. No. 10,898,515, which is a continuation of application No. 14/285,224, filed on May 22, 2014, now Pat. No. 10,555,970, which is a division of application No. 12/763,821, filed on Apr. 20, 2010, now Pat. No. 8,778,306.

(60) Provisional application No. 61/171,337, filed on Apr. 21, 2009.

(51) Int. Cl.
| | | |
|---|---|---|
| *A61K 33/14* | (2006.01) |
| *A23L 27/00* | (2016.01) |
| *A61K 9/00* | (2006.01) |
| *A61K 9/08* | (2006.01) |
| *A61K 9/48* | (2006.01) |
| *A61K 9/50* | (2006.01) |
| *A61K 31/194* | (2006.01) |
| *A61K 31/375* | (2006.01) |
| *A61K 31/77* | (2006.01) |
| *A61K 33/00* | (2006.01) |
| *A61K 33/04* | (2006.01) |
| *A61K 33/06* | (2006.01) |
| *A61K 47/02* | (2006.01) |
| *A61K 47/10* | (2017.01) |
| *A61P 1/10* | (2006.01) |
| *A61P 3/02* | (2006.01) |

(52) U.S. Cl.
CPC .............. *A61K 33/14* (2013.01); *A23L 27/88* (2016.08); *A61K 9/0095* (2013.01); *A61K 9/08* (2013.01); *A61K 9/48* (2013.01); *A61K 9/4808* (2013.01); *A61K 9/50* (2013.01); *A61K 31/194* (2013.01); *A61K 31/375* (2013.01); *A61K 31/77* (2013.01); *A61K 33/00* (2013.01); *A61K 33/04* (2013.01); *A61K 33/06* (2013.01); *A61K 47/02* (2013.01); *A61K 47/10* (2013.01); *A61P 1/10* (2018.01); *A61P 3/02* (2018.01)

(58) Field of Classification Search
CPC ........ A61K 33/14; A61K 9/0095; A61K 9/08; A61K 9/48; A61K 9/4808; A61K 9/50; A61K 31/194; A61K 31/375; A61K 31/77; A61K 33/00; A61K 33/04; A61K 33/06; A61K 47/02; A61K 47/10; A23L 27/88; A61P 1/10; A61P 3/02

See application file for complete search history.

(56) References Cited

U.S. PATENT DOCUMENTS

| | | |
|---|---|---|
| 5,164,192 A | 11/1992 | Louwes |
| 5,616,346 A | 4/1997 | Aronchick |
| 6,093,715 A * | 7/2000 | Harz ......................... A61P 3/02 |
| | | 544/251 |
| 6,447,763 B1 | 9/2002 | Gordon |
| 7,169,381 B2 | 1/2007 | Barras et al. |
| 7,332,184 B2 | 2/2008 | Vanner et al. |
| 7,582,283 B2 | 9/2009 | Taylor et al. |
| 7,687,075 B2 | 3/2010 | Skiendzielewski |
| 7,998,510 B2 * | 8/2011 | Caswell .................... A61P 1/00 |
| | | 424/606 |
| 2004/0143005 A1 | 7/2004 | Borody et al. |
| 2004/0192614 A1 | 9/2004 | Vanner et al. |
| 2005/0180921 A1 | 8/2005 | Taylor et al. |
| 2005/0271749 A1 | 12/2005 | Borody et al. |
| 2006/0068005 A1 | 3/2006 | Ross et al. |
| 2007/0098764 A1 | 5/2007 | Barras et al. |
| 2007/0196322 A1* | 8/2007 | Pelham ............. A61K 31/4402 |
| | | 424/78.01 |
| 2007/0207216 A1 | 9/2007 | Caswell |
| 2007/0298008 A1 | 12/2007 | Dennett et al. |

FOREIGN PATENT DOCUMENTS

| | | | |
|---|---|---|---|
| CN | 1312720 A | 9/2001 |
| CN | 1705494 A | 12/2005 |
| CN | 1950097 A | 4/2007 |
| EP | 0003679 A1 | 8/1979 |
| EP | 0396165 A1 | 11/1990 |
| JP | 02-270822 A1 | 11/1990 |
| JP | 02-292223 A | 12/1990 |
| JP | 2003-073260 | 3/2003 |
| WO | WO198700754 A1 | 2/1987 |
| WO | WO-9702744 A1 * | 1/1997 | ............. A01N 25/34 |
| WO | WO 00/48585 A1 | 8/2000 |
| WO | WO2006102364 A1 | 11/2006 |

OTHER PUBLICATIONS

"MoviPrep (PEG-3350, Sodium Suflate, Sodium Chloride, Potassium Chloride, Sodium Ascorbate and Ascorbic Acid for Oral Soluction)." FDA 2006. For Salix Pharmaceuticals, Inc.

(Continued)

*Primary Examiner* — Robert A Wax
*Assistant Examiner* — John Seungjai Kwon
(74) *Attorney, Agent, or Firm* — Casimir Jones, S.C.; David A. Casimir

(57) ABSTRACT

The present invention provides compositions, systems, kits, and methods for preparation prior to a colonoscopy or other gastrointestinal procedure. In particular, the present invention provides a colon lavage system comprising an aqueous portion and a solid portion.

20 Claims, No Drawings

(56) References Cited

OTHER PUBLICATIONS

Aoun et al., "A randomized single-blind trial of split-dose PEG-electrolyte solution without dietary restriction compared with whole dose PEG-electrolyte solution with dietary restriction for colonoscopy preparation," Gastrointest. Endosc. 2005; 62(2):213-8.
Cancer Prevention & Early Detection Facts and Figures 2006, American Cancer Society.
Davis et al., "Development of a lavage solution associated with minimal water and electrolyte absorption or secretion," Gastroenterology. 1980, 78:991-995.
Delegge et al., "Efficacy of bowel preparation with the use of a prepackaged, low fibre diet with a low sodium, magnesium citrate cathartic vs. a clear liquid diet with a standard sodium phosphate cathartic," Aliment Pharmacol Ther 2005; 21: 1491-1495.
Desmeules et al., "Acute phosphate nephropathy and renal failure," NEJM. 2003:349(10):1006-7.
Ernstoff et al., "A randomized blinded clinical trial of a rapid colonic lavage solution (Golytely) compared with standard preparation for colonoscopy and barium enema," Gastroenterology 1983:84:1512-6.
Fordtran et al., "A low-sodium solution for gastrointestinal lavage," Gastroenterology 1990:98:11-16.
Froehlich et al., "Impact of colonic cleansing on quality and diagnostic yield of colonoscopy: the European Panel of Appropriateness of Gastrointestinal Endoscopy European multicenter study," Gastrointest Endosc 2005; 61:378-84.
Hookey et al., "A prospective randomized trial comparing low-dose oral sodium phosphate plus stimulant laxatives with large volume polyethylene glycol solution for colon cleansing," Am J Gastroenterol. 2004; 99(11):2217-22.
Izzo et al., "Nitric oxide as a mediator of the laxative action of magnesium sulphate," Br J Pharmacol. Sep. 1994; 113(1):228-32.
Lichtenstein et al., "Clinical trial: sodium phosphate tablets are preferred and better tolerated by patients compared to polyethylene glycol solution plus bisacodyl tablets for bowel prep," Aliment Pharmacol Ther. 2007; 26(10):1361-1370.
Maciosek et al., "Priorities Among Effective Clinical Preventive Services: Results of a Systematic Review and Analysis," Am J Prev Med, 2006, 31:52-61.
Markowitz et al., "Acute phosphate nephropathy following oral sodium phosphate bowel purgative: an underrecognized cause of chronic renal failure," J Am Soc Nephrol 2005;16:3389-96.
Ogawa et al., "Stability on Pharmaceutical Preparation and Bacterial Contamination of Oral Gastrointestinal Lavage Solution." Byoin Yakugaku (Hospital Pharmacy) 1991, 17(6):482-489.
Rapier et al., "A prospective study to assess the efficacy and patient tolerance of three bowel preparations for colonoscopy," Gastroenterology Nursing 2006; 29(4):305-308.
Rex et al., "Impact of bowel preparation on efficiency and cost of colonoscopy," Am J Gastroenterol, 2002; 97:1696-1700.
Scott et al., "Efficacy and tolerance of sodium phosphates oral solution after diet liberalization," Gastroenterol. Nurs. 2005; 28:133-139.
Wexner et al., "A concensus document on bowel preparation prior to colonoscopy" Practice/Clinical Guidelines published Apr. 2006, pp. 1-25.
"Summary of product characteristics: Laxido Orange, powder for oral solution." Nov. 10, 2008, pp. 1-5.
ASGE Technology Committee et al., "Colonoscopy preparation." Gastrointestinal Endoscopy Jun. 1, 2009, Elsevier, NL, 69(7): 1201-1209.
Pashankar et al., "Polyethylene Glycol 3350 Without Electrolytes: A new safe, effective, and palatable bowel preparation for colonscopy in children." Journal of Pediatrics Mar. 2004, 144(3): 358-362.

* cited by examiner

COLON LAVAGE SYSTEM

The present application is a continuation of U.S. application Ser. No. 16/786,541, filed Feb. 10, 2020, which is a continuation of U.S. application Ser. No. 14/285,224, filed May 22, 2014, now U.S. Pat. No. 10,555,970, issued Feb. 11, 2020, which is divisional of U.S. patent application Ser. No. 12/763,821, filed Apr. 20, 2010, now U.S. Pat. No. 8,778,306, issued Jul. 15, 2014, which claims priority to U.S. Provisional Patent Application Ser. No. 61/171,337, filed Apr. 21, 2009, each of which are herein incorporated by reference in its entirety.

FIELD OF THE INVENTION

The present invention provides compositions, systems, kits, and methods for preparation prior to a colonoscopy or other gastrointestinal procedure. In particular, the present invention provides a colon lavage system comprising an aqueous portion and a solid portion.

BACKGROUND OF THE INVENTION

Screening colonoscopy is seen as delivering among the best returns on public investment (Maciosek et al. Am T Prev Med 2006; 31:52-61., herein incorporated by reference in its entirety). Despite a growing body of data, only half of adults in the United States for whom a colonoscopy is recommended undergo the procedure (Cancer Prevention & Early Detection Facts and FIGS. 2006, American Cancer Society, herein incorporated by reference in its entirety). One of the major barriers to compliance is the unpleasantness of the preparation procedure (aka gastrointestinal lavage, colon gavage, colonoscopy prep, etc.))(Harewood et al. Am J Gastroenterol 2002; 97: 3186-94, herein incorporated by reference in its entirety). Preparation of the colon for optical colonoscopy is important for an accurate and efficient exam. It is not surprising that poor preps result in higher miss rates for significant lesions (Froehlich et al. Gastrointest Endosc 2005; 61:378-84, herein incorporated by reference in its entirety), and are a major cause of lengthier, time-consuming exams (Rex et al. Am J Gastroenterol 2002; 97:1698-1700., herein incorporated by reference in its entirety).

There are a number of ways to cleanse the colon, each with advantages and disadvantages. The physician must balance the factors of patient safety, patient tolerability, and quality of the prep. For example, growing data on the risks of sodium phosphate preps has tempered enthusiasm for these types preps. Purgatives can be based on magnesium salts, sodium phosphate, or buffered saline solution with polyethylene glycol (PEG). Bisacodyl is sometimes added to the regimen to stimulate colonic motility. The downside of adding Bisacodyl to a cleansing regimen is that it may cause additional nausea and cramps. An overview of the current state of colonoscopy prep products is as follows:

Magnesium Salt Preparations

Magnesium salts, such as Magnesium Citrate are known to stimulate colonic mucosal ion secretion (Izzo et al. Br J Pharmacol. 1994 September; 113(1):228-32, herein incorporated by reference in its entirety). Few gastroenterologists still use over-the-counter Magnesium Citrate solution as a prep. The only Magnesium-based solution designed for colonoscopy preparation is the LOSO PREP, a proprietary kit marketed by the EZ-EM Corporation. Magnesium Citrate is provided as a dry powder in a pre-measured pouch that is reconstituted with water or as a concentrated solution that is diluted before use. It is marketed with four 5 mg Bisacodyl tablets to take during the prep and a single 10 mg Bisacodyl suppository to use the morning of the procedure. Studies have examined its efficacy as bowel prep and show results similar to PEG-based preps with better tolerability (Delegge et al. Aliment Pharmacol Ther 2005; 21: 1491-1495., Rapier et al. Gastroenterology Nursing 2006; 29(4):305-308., herein incorporated by reference in their entireties). This has been studied in combination with an extremely low residue diet (NUTRA PREP, EZ-EM Corporation) with similar results. Electrolyte imbalances can occur if sufficient clear liquids are not consumed during the prep.

Sodium Phosphate Preparations

Sodium phosphate works as an osmotic agent and draws fluid into the colon, resulting in a purgative effect. Sodium Phosphate can be given as a solution (FLEET PHOSPHO-SODA EZ-PREP) or as tablets (VISICOL ANI) OSMO-PREP). They are among the best tolerated colon preps from a patient's point of view (Hockey et al. Am J Gastroenterol. 2004; 99(11):2217-22, Lichtenstein et al. Aliment Phannacol Ther. 2007; 26(10):1361-1370., herein incorporated by reference in their entireties). It is critical for patients to drink sufficient quantities of clear liquids during these preps to ensure that the cathartic effect does not dehydrate them during the prep. The FLEET PHOSPHO-SODA PREP instructs patients to drink 24 ounces of fluid with the first dose of PHOSPHO-SODA, at least 24 ounces of clear liquids in between doses, and 24 ounces with the second dose. Patients who do not drink at least the required 2.1 liters of fluid during their prep are at significant risk of renal and electrolyte problems as a result of the prep.

During routine use of sodium phosphate preps, some of the phosphate is absorbed, and there is growing evidence that this may damage the kidney. Beginning in 2003, reports began to emerge about acute and chronic phosphate nephropathy in patients receiving phosphate-based preps, namely FLEETS PHOSPHO-SODA and VISICOL (Desmeules et al. NEJM, 200:349(10):1006-7., herein incorporated by reference in its entirety). The FDA now lists on their website more than thirty cases of renal injury associated with the use of phosphate salts for colon preparation. The FDA reports were associated with higher dosing regimens for phosphate preps (60 or more grams of sodium phosphate). No reports were received regarding the use of OSMOPREP®, which contains 48 grams of sodium phosphate. All regimens have now been brought below 60 grams of sodium phosphate. More recent studies in the Nephrology literature describe a relative risk for acute kidney injury at 1.5 to 3.6 times that of controls in those patients who have taken a phosphate-based colon prep (Markowitz et al. J Am Soc Nephrol 2005; 16:3389-96, herein incorporated by reference in its entirety). Patients who are at increased risk for this complication include people over the age of 57, and those with significant co-morbidity including hypertension, pre-existing CKD, and those patients taking either angiotensin converting enzyme (ACE) inhibitors or angiotensin receptor blockers (ARB). Because of the problems arising with sodium phosphate preps, training programs such as Mayo Clinic and University of Pennsylvania have relegated these preps to secondary status. Most recently, in December 2008, the FDA applied black-box warnings to VISICOL and OSMOPREP to highlight the risk for serious renal injury. Shortly after that, the C.B. Fleet Company voluntarily withdrew FLEETS PHOSPHO-SODA from the market due to its risk for renal injury when used as a colon prep.

Polyethylene Glycol (PEG) Preparations

Buffered saline solutions with PEG have been available for almost thirty years. While providing less risk to the patient with regard to fluid and electrolyte balance, the sheer volume of fluid to drink coupled with the poor palatability of some of these solutions have made them unpopular among the initiated. PEG based products are marketed under a variety of trade names (GO-LYTELY, COLYTE, NULYTELY, HALFLYTELY, GLYCOPREP, and MOVIPREP (see e.g., U.S. Pat. No. 7,169,381, herein incorporated by reference in its entirety)). COLYTE and GOLYTELY are the prototypical 4-liter colon gavage preps. The salty taste, nausea, and cramps cause the majority of patient complaints. NULYTELY was formulated as an improvement over GOLYTELY® with the deletion of Sulfate as an osmotic agent, increasing the PEG concentration to increase its osmotic effect, and the addition of flavor packs to improve palatability. The volume remains 4 liters. The latest iterations of PEG-based preps are tiALFLYTELY and MOVIPREP. Both are 2-liter prep solutions. HALFLYTELY is marketed with two 5 mg Bisacodyl tablets to take during the prep to enhance colonic emptying. MOVIPREP does not require Bisacodyl but does require an additional liter of clear liquid be consumed during the prep. In general, the 2-liter PEG preps are better tolerated but not quite as cleansing as the 4 liter PEG preps.

One trend that is gaining popularity is the split-dosing schedule, wherein only half of the prep is taken the night before the procedure, and the remainder is taken early in the morning prior to the procedure. The split schedule improves tolerability for patients (Aoun et al. Gastrointest. Endosc. 2005; 62(2):213-8., herein incorporated by reference in its entirety). The diminished volume of any one dose reduces nausea and cramps. Ileal effluent (mucous, bile, and sloughed cells) may accumulate in the cecum and right colon overnight after completion of a prep. This material is often washed away by the morning dose in the split dose schedule. The split schedule requires that the patient get up early to take their morning dose 3 to 5 hours prior to their procedure. Some of the newer preps are designed as a split dose (FLEET'S PHOSPHO-SODA, VISICOL, OSMOPREP, and MOVIPREP). The 4-liter PEG preps can also be given as a split dose, usually 3 liters in the evening and 1 liter in the early morning.

Improving the diet prior to and during the prep may improve patient tolerance. There is some data indicating that the use of extremely low residue diets during the day of the prep (the day prior to the colonoscopy) instead of a clear liquid diet only may improve the tolerability of the regimen without diminishing the quality of colonic cleansing (Scott et al. Gastroenterol. Nurs, 2005; 28:133-139, herein incorporated by reference in its entirety). A pre-packaged low residue diet is marketed by E-Z-EM under the label NUTRA-PREP.

Typical gastrointestinal lavage formulations are described in US Pat. App. No. 2007/0098764, US Pat. App. No. 2007/0298008, Fordtran et al. Gastroenterology 1990:98:11-16., Ernstoff et al. Gastroenterology 1983:84:1512-6., Davis et al. Gastroenterology. 1980:78:991-995., herein incorporated by reference in their entireties.

What are needed are improved systems and methods that improve patient tolerance and maintain safety and efficacy.

SUMMARY

In some embodiments, the present invention provides a kit comprising a plurality of individually packaged doses of a palatable osmotic agent, to be administered in aqueous solution, and a plurality of doses of electrolytes. In some embodiments, the osmotic agent comprises PEG. In some embodiments, the electrolytes comprise sodium bicarbonate, sodium chloride, and potassium chloride. In some embodiments, the electrolytes further comprise sodium sulfate. In some embodiments, the electrolytes comprise ascorbic acid and/or sodium ascorbate. In some embodiments, the electrolytes further comprise salts of magnesium, such as magnesium sulfate or magnesium citrate. In some embodiments, the plurality of doses of electrolytes comprises pills, capsules, tablets, gel-caps, gel-caps filled with a paste or suspension, micro-encapsulated salts for administration as a capsule or suspended in a liquid. In some embodiments, a kit of the present invention further comprises a plurality of flavored drink mix doses or other flavorant packages. In some embodiments, the plurality of individually packaged doses of palatable osmotic agent comprises 4-12 doses of osmotic agent, although higher or lower amounts may be used. In some embodiments, the plurality of doses of electrolytes comprises 2-8 doses per dose of osmotic agent, although higher or lower amounts may be used.

In some embodiments, the present invention provides a method for preparing a subject for a colon-related procedure comprising one or more of the steps of: (a) providing a plurality of individually packaged osmotic agent doses and a plurality of individually packaged electrolyte doses, (b) dissolving one or more of a plurality of osmotic agent doses in water or other solvent (e.g., other aqueous solvent), (c) administering one or more of the plurality of osmotic agent doses dissolved in water or other solvent to a subject, (d) administering one or more of a plurality of electrolyte doses to a subject, (e) repeating steps (b)-(d) until all of the plurality of osmotic agent doses and all of the plurality of electrolyte doses have been ingested by the subject, (f) passing stool from the colon of said subject. (g) analyzing stool from the subject, and (h) carrying out a diagnostic or surgical procedure on the subject. In some embodiments, the method comprises or consists of steps (a)-(e). In some embodiments, the palatable osmotic agent comprises PEG. In some embodiments, the electrolytes comprise sodium bicarbonate, sodium chloride, and potassium chloride. In some embodiments, the electrolytes further comprise sodium sulfate. In some embodiments, the electrolytes comprise ascorbic acid and/or sodium ascorbate. In some embodiments, the electrolytes further comprise salts of magnesium, such as magnesium sulfate or magnesium citrate. In some embodiments, the plurality of doses of electrolytes comprises pills, capsules, tablets, gel-caps, gel-caps filled with a paste or suspension, micro-encapsulated salts for administration as a capsule or suspended in a liquid. In some embodiments, a method of the present invention further comprises providing a plurality of flavorant packages, including flavored drink mix doses, wherein the flavor mix is dissolved in water or other solvent with the plurality of purgative doses. In some embodiments, passing stool from the colon of the subject comprises evacuating the colon of digested or undigested food and stool.

DETAILED DESCRIPTION OF EMBODIMENTS

In some embodiments, the present invention provides compositions, systems, kits, and methods for patient preparation prior to a colon-related medical procedure (e.g. colonoscopy). In particular, in some embodiments, the present invention provides a colon lavage system comprising an aqueous portion and a solid portion. In some embodiments, the present invention provides a colon lavage system that employs both aqueous solution and capsules or pills or tablets or other delivery modes to improve palatability over current PEG (polyethylene glycol)-based preps and improve safety over current tablet preps. In some embodiments, the present invention provides improved patient compliance with colon-prep procedure. In some embodiments, the present invention provides improved accuracy for colonoscopy and other gastrointestinal procedures. In some embodiments, the present invention provides a multi-component system (e.g. 2 components. 3 components, greater than 3 components, etc.). In some embodiments, the present invention provides two components: (1) a palatable osmotic agent, and (2) an electrolyte component. In some embodiments, the present invention provides two components: (1) a plurality of osmotic agent doses, and (2) a plurality electrolyte doses. In some embodiments, the present invention provides two components: (1) an aqueous PEG solution, and (2) salt pills. In some embodiments, the salt pills may contain electrolytes that may act as an osmotic agent in the gut, such as sulfate salts and/or magnesium salts.

In some embodiments, the present invention provides a palatable osmotic agent component. In some embodiments, the present invention provides a stimulant, lubricant, and/or saline laxatives to evacuate the colon. In some embodiments, an additional purgative of the present invention may be selected from, but is not limited to bulk-producing agents, stool softeners, surfactants, lubricants, emollients, hydrating agents, osmotics, saline solutions, hyperosmotics (e.g. PEG), stimulants, irritants, serotonin agonists, etc. In some embodiments, the present invention serves to hasten the elimination of digested and undigested remains of food in the large intestine and colon. In some embodiments, the purgative of the present invention is configured to induce bowel movement in a desired time (e.g. <30 minutes, 1 hour, 2 hours, 3 hours, 4 hours, 5 hours, 6 hours, 7 hours, 8 hours, 9 hours, 10 hours, 11 hours, 12 hours, >12 hours, etc.).

In some embodiments, the palatable osmotic agent component of present invention is a polyethylene glycol (PEG) component. In some embodiments, the present invention comprises a polyethylene oxide) (PEO) or polyoxyethylene (POE) component. In some embodiments, PEG oligomers and/or polymers of the present invention have a molecular weight or average molecular weight below 20,000 g/mol (e.g. <20000 g/mol, <15000 L.);/mol, <12000 g/mol, <10000 g/mol, <8000 g/mol, <6,000 L.);/mol, <4,000 g/mol, <2000 g/mol, <1000 g/mol, etc.). In some embodiments, the PEG oligomers and/or polymers of the present invention have a molecular weight or average molecular weight above 105 g/mol (e.g. >200 g/mol, >300 g/mol, >400 g/mol, >500 g/mol, >750 g/mol, >1000 g/mol, >2000 g/mol, >4000 g/mol, >6000 g/mol, etc.). In some embodiments, the PEG oligomers and/or polymers of the present invention have a molecular weight or average molecular weight greater than or equal to 1450 daltons and less than or equal to 8000 daltons. In some embodiments, the PEG oligomers and/or polymers of the present invention have a molecular weight or average molecular weight of approximately 3350 daltons or of 3350 daltons. In some embodiments, the present invention provides PEG dissolved in water or aqueous solution. In some embodiments, the present invention provides thy PEG configured to be dissolved in water or aqueous solution. In some embodiments, the present invention provides a concentrated. PEG solution configured to be diluted in water or aqueous solution. In some embodiments, PEG of the present invention is low toxicity. In some embodiments, the PEG component of the present invention serves as a laxative and/or purgative (e.g. taken to induce bowel movements and/or to loosen the stool). In some embodiments, PEG is a hyperosmotic agent. In some embodiments, the purgative component consists of PEG in either dry, power form or dissolved in water (i.e., consists of PEG and water).

In some embodiments, the palatable osmotic agent component does not contain salt or is substantially free of salt. In some embodiments, the palatable osmotic agent component does not contain any salt other than salt that is provided as part of the PEG component (e.g., as a byproduct of PEG manufacture). In some embodiments, the palatable osmotic agent component is free from or substantially free from or functionally free (i.e., salts are present at a concentration insufficient to elicit a benefit to colon lavage procedures) from one or more of the salts: sodium sulfate, sodium bicarbonate, sodium chloride, sodium phosphate((e.g. monosodium phosphate, disodium phosphate, tri sodium phosphate, etc.) potassium bicarbonate, potassium chloride, potassium phosphate, potassium sulfate, magnesium sulfate, magnesium bicarbonate, magnesium chloride, magnesium phosphates, calcium bicarbonate, calcium chloride, calcium phosphate, calcium sulfate, ascorbic acid, and sodium ascorbate.

In some embodiments, the present invention provides an electrolyte component. In some embodiments, the electrolyte component comprises or consists of one or more salts. In some embodiments, the electrolyte component is provided in a solid form suitable for oral administration in solid form. In some embodiments, the electrolyte component of the present invention comprises one or more cations (e.g., sodium, potassium, magnesium, calcium, etc.). In some embodiments, the electrolyte component comprises the anions (e.g., bicarbonate, chloride, phosphate, sulfate, etc.). In some embodiments, the electrolyte component comprises or consists of sodium bicarbonate, sodium chloride, and potassium chloride. In some embodiments, the electrolyte component comprises or consists of sodium sulfate, sodium bicarbonate, sodium chloride, and potassium chloride. In some embodiments, the electrolyte component of the present invention comprises or consists of sodium sulfate, sodium bicarbonate, sodium chloride, sodium phosphate (e.g. monosodium phosphate, disodium phosphate, tri sodium phosphate, etc.), potassium bicarbonate, potassium chloride, potassium phosphate, potassium sulfate, magnesium sulfate, magnesium bicarbonate, magnesium chloride, magnesium phosphates, calcium bicarbonate, calcium chloride, calcium phosphate, calcium sulfate, ascorbic acid, sodium ascorbate, etc. In some embodiments, the electrolyte component comprises 30 grams or less Sodium sulfate in tablet/'capsule form to be ingested with each liter of aqueous osmotic agent (e.g. 30 grams . . . 25 grams . . . 20 grams . . . 15 grams . . . 10 grams . . . 5 grams . . . 0 grams, etc.). In some embodiments, the electrolyte component comprises 10 grams or less Sodium bicarbonate in tablet/capsule form to be ingested with each liter of aqueous purgative (e.g. 10 grams . . . 8 grams . . . 6 grams . . . 4 grams, 0.2 grams . . . 0 grams, etc.). In some embodiments, the electrolyte component comprises 20 grams or less Sodium chloride in tablet/capsule form to be ingested with each liter of aqueous purgative (e.g. 20 grams . . . 16 grams, 12 grams . . . 8 grams . . . 4 grams . . . 0 grams, etc.). In some embodiments, the electrolyte component comprises 5 gram or less Potassium chloride in tablet/capsule form to be ingested with each liter of aqueous purgative (e.g. 5 gram . . . 4 grams . . . 3 grams . . . 2 grams . . . 1 grams, 0 grams, etc.). In some embodiments, the electrolyte component comprises 20 grams or less Sodium ascorbate in tablet/capsule form to be ingested with each liter of aqueous purgative (e.g. 20 grams . . . 16 grams . . . 12 grams . . . 8 grams . . . 4 grams . . . 0 grams, etc.). In some embodiments, the electrolyte component comprises 20 grams or less Ascorbic acid in tablet/capsule form to be ingested with each liter of aqueous purgative (e.g. 20 grams . . . 16 grams . . . 12 grams, 0.8 grams . . . 4 grams . . . 0 grams, etc.). In some embodiments, the electrolyte component comprises 10 grams or less Magnesium citrate in tablet/capsule form to be ingested with each liter of aqueous purgative (e.g. 10 grams . . . 8 grams . . . 6 grams . . . 4 grams . . . 2 grams . . . 0 grams, etc.). In some embodiments, the electrolyte component comprises 100 grams or less salt in tablet/capsule form to be ingested with each liter of aqueous purgative (e.g. 100 grams . . . 80 grams . . . 60 grams . . . 40 grams . . . 20 grams . . . 0 grams, etc.). In some embodiments, the electrolyte component is configured to maintain proper electrolyte levels in a subject undergoing a colon lavage procedure. In some embodiments, the electrolyte component is configured to maintain proper electrolyte levels in a subject undergoing purgative preparation for colonoscopy. In some embodiments, the electrolyte component is administered in a series of doses and is configured to mix in the stomach of the subject. In some embodiments, the electrolyte component is configured to mix in the stomach of a subject to provide an electrolyte solution which is approximately iso-osmotic with plasma (e.g. 230 mM to 330 mM, 270 mM to 290 mM, 280 mM, etc.). In some embodiments, the electrolyte component is configured to mix in the stomach of a subject to provide an electrolyte solution which is slightly hyper-osmolar with plasma (e.g. 280 mM to 400 mM, etc.). In some embodiments, each dose of electrolytes (e.g. tablet, capsule, pill, etc.) comprises 300 mg to 1000 mg of solid material (e.g. electrolytes, filler, etc.) per dose (e.g. 300 mg . . . 400 mg . . . 500 mg . . . 600 mg . . . 700 mg, 800 mg . . . 900 mg . . . 1000 mg, etc.). In some embodiments, the mass or volume of solid material per dose is selected to reach a balance between number of doses and size of doses to be administered to a subject. In some embodiments, the electrolyte component is marketed as capsules, tablets, gel-caps, etc. to be combined by the purchaser with an over-the-counter osmotic agent such as PEG 3350.

In some embodiments, the present invention provides a palatable osmotic agent component and an electrolyte component in ingestible doses. In some embodiments, the osmotic agent (e.g. PEG) is provided in a dry form (e.g. powder, granular, etc). In some embodiments, the osmotic agent (e.g. PEG) is provided in a thy volume configured to be dissolved in a solvent (e.g. water). In some embodiments, the osmotic agent (e.g. PEG) is provided in a dry volume configured to be dissolved in a convenient volume (e.g. 250 ml, 500 ml, 1 L, 8 ounces, 16 ounces, 24 ounces, etc.) of solvent (e.g. water). In some embodiments, the osmotic agent (e.g. PEG) is provided in aliquots based on weight (e.g. 5 grams, 10 grams . . . 15 grams . . . 20 grams, 25 grams . . . :29.5 grams . . . 35 grams . . . 40 grams . . . 45 grams . . . 50 grams . . . 55 grams . . . 60 grams . . . etc.). In some embodiments, an amount of osmotic agent (e.g. PEG) is configured to be dissolved in a specified volume of water (e.g. 15 grams PEG in 8 ounces of water, 29.5 grams of PEG in 500 ml of water, 52.5 grams of PEG in 500 ml water, 60 grams of PEG in 1 L of water, etc.). In some embodiments, the palatable osmotic agent (e.g. PEG) can be dissolved in more solvent (e.g. water) to create less concentrated solution to better mask the presence of the osmotic agent in the solution. In some embodiments, the osmotic agent (e.g. PEG) can be dissolved in less solvent (e.g. water) to create more concentrated solution so a subject can drink a smaller volume of liquid. In some embodiments, a volume of osmotic agent (e.g. PEG) is dissolved in a volume of solvent (e.g. water) appropriate for eliciting the desired purging effect. In some embodiments, the present invention provides a plurality of doses of osmotic agent, each to be dissolved in separate volumes of solvent (e.g. 2 doses, 3 doses, 4 doses, 5 doses, 6 doses, 7 doses, 8 doses, 9 doses, 10 doses, >10 doses, etc.). In some embodiments, the cumulative amount of the provided doses is equal to the total amount of osmotic agent to be taken in a prep (e.g., 4 liters, 3 liters, 2 liters, etc.).

In some embodiments, the present invention provides a flavorant. The flavorant may be formulated as part of the osmotic agent component. Likewise, the flavorant may be provided separately and mixed with the osmotic agent component prior to administration. The flavorant may be provided as a solid (e.g., powder) or may be a liquid. In some embodiments, the flavorant is provided in liquid form and acts as the liquid carrier for delivery of the osmotic agent component. In some embodiments, dry, osmotic agent component (e.g., PEG) and dry flavorant are added to water prior to administration. The present invention is not limited by the nature of the flavorant. In some embodiments, the flavorant is a commercially available drink mix material (e.g. CRYSTAL LIGHT, HI-C, similar drink mixes, etc.). In some embodiments, the present invention provides a plurality of flavored drink mix aliquots in individual packages. In some embodiments, individual packages of flavored drink mix are configured to flavor a volume of water. In some embodiments, individual packages of flavored drink mix are configured to flavor a volume of water corresponding to the volume of water required to dissolve a dose of osmotic agent (e.g. PEG) provided by the present invention (e.g. 250 ml . . . 500 ml . . . 1000 ml . . . 2000 ml . . . 4000 ml . . . etc.). In some embodiments, flavored drink mix produces a flavored drink when dissolved in an appropriate volume of water. In some embodiments, flavored drink mix makes thinking water (e.g. a large volume of water, water with dissolved osmotic agent, etc.) more acceptable (e.g. palatable, enjoyable, etc.) to a subject. In some embodiments, flavored drink mix can be provided in any suitable flavor (e.g. cherry, strawberry, watermelon, grape, lemon-lime, banana, iced tea, lemonade, apple, orange, etc.). In some embodiments, the present invention provides a variety of different flavors of flavored drink mix to allow a subject to flavor successive doses of osmotic agent dissolved in water with different flavors, reducing or avoiding taste fatigue. In some embodiments, flavored water with dissolved osmotic agent is indistinguishable or nearly undistinguishable from flavored water without dissolved osmotic agent (e.g. PEG). In some embodiments, other components, such as colorants, alcohol, or medications are provided with the osmotic agent administration.

In some embodiments, the present invention provides individually packaged doses of PEG (e.g. 29.5 grams) that can be dissolved into 0.5 liters of water (e.g. standard sized water bottle). In some embodiments, the above PEG and water solution is consumed with or without flavoring (e.g. CRYSTAL LITE or similar). In some embodiments, a plurality of doses (e.g. 29.5 grams of PEG in 0.5 liters of water) are consumed to yield a total volume which is appropriate for a patients size, age, health, and/or physical characteristics (e.g. 1 liter (2 doses), 1.5 liters (3 doses), 2 liters (4 doses), 2.5 liters (5 doses). 3 liters (6 doses), 3.5 liters (7 doses), 4 liters (8 doses), 4.5 liters (9 doses), 5 liters (10 doses), 5.5 liters (11 doses), 6 liters (12 doses), 6.5 liters (13 doses), 7 liters (14 doses), 7.5 liters (16 doses), 8 liters (16 doses), 8.5 liters (1 doses), 9 liters (18 doses), 9.5 liters (19 doses), 10 liters (20 doses), >10 liters (>20 doses), etc.). In some embodiments, the present invention provides individually packaged doses of PEG (e.g. 52.5 grams) that can be dissolved into 0.5 liters of water (e.g. standard sized water bottle). In some embodiments, the above PEG and water solution is consumed with or without flavoring (e.g. CRYSTAL LITE or similar). In some embodiments, a plurality of doses (e.g. 29.5 grams of PEG in 0.5 liters of water) are consumed to yield a total volume which is appropriate for a patients size, age, health, and/or physical characteristics (e.g. 1 liter (2 doses), 1.5 liters (3 doses), 2 liters (4 doses), 2.5 liters (5 doses), 3 liters (6 doses), 3.5 liters (7 doses), 4 liters (8 doses), 4.5 liters (9 doses), 5 liters (10 doses), 5.5 liters (11 doses), 6 liters (12 doses), 6.5 liters (13 doses), 7 liters (14 doses), 7.5 liters (16 doses), 8 liters (16 doses), 8.5 liters (17 doses), 9 liters (18 doses), 9.5 liters (19 doses), 10 liters (20 doses), >10 liters (>20 doses), etc.). In some embodiments, PEG dose size and water volume are adjusted for ease of packaging, marketing, ingestion, etc. In some embodiments, the number of doses (e.g., half liter doses) is selected for a patient based on their size, age, gender, etc. Thus, in some embodiments, some patients are not required to consume 4 liters of product, but can consume a lesser, more palatable amount.

In some embodiments, the present invention provides capsules, pills, gel-caps, micro-encapsulated granules, or tablets containing salts selected from but not limited to sodium sulfate, sodium bicarbonate, sodium chloride, and potassium chloride. In some embodiments, a preselected number of salt doses (e.g. capsules, etc.) are ingested by a subject with each dose of dissolved osmotic agent (e.g. PEG solution) (e.g. 1 salt dose/1 PEG dose, 2 salt doses/1 PEG dose, 2 salt doses/i PEG dose, 3 salt doses/i PEG dose, 4 salt doses/1 PEG dose, 5 salt doses/1. PEG dose, 6 salt doses/1 PEG dose, 7 salt doses/1 PEG dose, 8 salt doses/i PEG dose, 9 salt doses/1 PEG dose, 10 salt doses/1 PEG dose, >10 salt doses/1 PEG dose, etc.). In some embodiments, a preselected number of salt doses (e.g. capsules, etc.) are ingested by a subject with each 0.5 liter dose of PEG solution. In some embodiments, mixing of the PEG and salts occurs in the stomach producing a PEG and salt solution. In some embodiments, a PEG and salt solution produced by mixing a plurality of osmotic agent components((e.g. PEG component) and a plurality of salt components (e.g. electrolytes) with the specified volume of water results in a solution of similar or identical makeup and concentration to standard formulations in use (e.g. MOVIPREP, GOLYTELY, NULYTELY, etc.).

In some embodiments, commonly used or standard formulations of osmotic agent and salt solutions comprise 100 g/L PEG-3350, 7.5 g/L sodium sulfate, 2.69 g/L sodium chloride, and 1.015 g/L potassium chloride. In some embodiments, the proceeding concentrations are present in 0.5 L, 1.0 L, or 2 L doses. In some embodiments, commonly used or standard formulations of purgative and salt solutions comprise 60 g/L PEG-3350, 5.68 g/L sodium sulfate, 1.46 g/L sodium chloride, 1.68 g/L sodium bicarbonate, and 0.745 g/L potassium chloride. In some embodiments, the proceeding concentrations are present in 0.5 L, 1.0 L, or 2 L doses. In some embodiments, a mixed solution of commonly used or standard formulations of PEG and electrolytes comprises 125 mEq/L sodium, 10 mEq/L potassium, 20 mEq/L bicarbonate, 80 mEq/L sulfate, 35 mEq/L chloride, and 18 mEq/L polyethylene glycol-3350.

In some embodiments, the present invention provides compositions, systems, kits; and methods for patient preparation prior to a colon-related or gastrointestinal medical procedure. In some embodiments, the present invention provides compositions, systems, kits, and methods for use preparative use prior to gastrointestinal procedures including but not limited to colonoscopy, capsule endoscopy, single- and double-balloon enteroscopy, endoluminal gastroplication, endoscopic ultrasound (EUS), esophagogastroduodenoscopy (EGD), endoscopic retrograde cholangiopancreatography (ERCP), esophageal pH exam, flexible sigmoidoscopy (Flex Sig), hydrogen breath test, liver biopsy, percutaneous endoscopic gastrostomy (PEG), biofeedback for anorectal dysfunction; intraoperative radiation therapy (TORT), diagnostic GI radiology, including barium enema, CT colonography, CT enterography, MR colonography, and MR enterography; surgical procedures including, but not limited to laparoscopic cholecystectomy (Gallbladder Removal), colectomy, hysterectomy, hemorrhoidectomy, herniorrhaphy, and NOTES (natural orifice transluminal endoscopic surgery).

In some embodiments, the present invention provides compositions, systems, kits, and methods for clearing digested and/or undigested food and/or stool from the colon and/or other portions of the gastrointestinal for health reasons, to restore health, to remove toxins (e.g. pollution, secondary smoking, harmful chemicals, pesticides, etc.), as a remedy for ailments (e.g. constipation, hepatic encephalopathy, acne, *candida*, brain fog, sluggishness, colonic dysenertia, encopresis, constipative-predominant irritable bowel syndrome (IBS-C)), and to prevent disease. In some embodiments, a subject being administered a composition, system, kit, or method of the present invention is a human (e.g. patient), animal, mammal, equine, bovine, cat dog, non human primate, rodent, etc.

In some embodiments, a composition, system, kits and/or method of the present invention may provided in any suitable manner or packaging. In some embodiments, the palatable osmotic agent is provided in granular or powder form in doses ready to be dissolved in clear liquid (e.g. water or flavored drink). In some embodiments, doses of osmotic agent are pre-measured. In some embodiments, doses of osmotic agent are provided in doses to be dissolved in a specified volume of clear liquid (e.g. 250 ml . . . 500 ml . . . 1000 ml, 1500 ml, 0.2000 ml, etc.). In some embodiments, does of purgative are provided in individual bags, blister packs, cups, bottles, jars, envelopes, and/or containers, etc. In some embodiments, doses of osmotic agent are provided in a single container with multiple compartments. In some embodiments, a specific number of doses of purgative are provided in a kit or package according to patient specific criteria (e.g. age, size, weight, sex, medical condition, species, etc). In some embodiments, the number of osmotic agent doses are prepared and/or assembled by a pharmacist based on clinician and/or manufacturer instructions. In some embodiments, the number of osmotic agent (e.g., PEG) doses are preassembled into kits and/or packages, and a proper kit or package is selected for a subject based on subject specific criteria (e.g. age, size, weight, sex, medical condition, species, etc.).

In some embodiments, electrolytes of the present invention are provided in a plurality of individual doses (e.g. pills, capsules, tablets, etc.). In some embodiments, electrolyte doses are manufactured by combining the desired salts with a known carrier to form a solid preparation suitable for oral administration. In general, these compounds are formulated with a pharmacologically acceptable liquid or solid carrier, and a solvent, a dispersant, an emulsifier, a buffer, a stabilizer, an excipient, a binder, a disintegrant, a lubricant, or the like is added thereto as desired, so that a solid agent such as a tablet, a granule, a powder, a fine powder, and a capsule, dry agent or a liquid agent. The carrier can be selected depending upon the administration form and preparation form of the electrolyte dose. In the case of an orally administered preparation comprising a solid composition, the preparation can be produced in the form of a tablet, a pill, a capsule, a powder, a fine powder, a granule, a suspension contained within a gel-cap, or the like. In some embodiments, the electrolytes are combined with, for example, starch, lactose, saccharose, mannitol, carboxymethyl cellulose, cornstarch, an inorganic salt, or the like to aid in ease of administration. In addition, during the preparation of the orally, administered preparation, a binder, a disintegrant, a surfactant, a lubricant, a fluidity accelerator, a flavor, a colorant, a perfume, and the like can be further formulated. Preferably, the salt isolated in manner so as not to elicit a taste response from the subject. For example, digestible capsules may be used to isolate the salt until reaching the stomach. In the case of forming into a tablet or pill, electrolytes and accessory compounds or additives are pressed into a tablet or pill of a suitable size for oral administration. In the case of forming into a tablet or pill, for example, the tablet or pill may be covered with a sugar-coating made of sucrose, gelatin or hydroxypropyl cellulose, or with a film made of a substance soluble in the stomach or intestine as desired. In the case of a capsule, the electrolytes and any additional carriers and/or compounds are contained in a plurality of synthetic capsules of suitable size for oral administration. Capsules dissolve upon entry into gastric juices, thereby releasing the electrolytes into the stomach.

In some embodiments, electrolytes of the present invention are provided in a plurality of individual doses (e.g. pills, capsules, tablets, etc.). In some embodiments, doses of electrolytes are provided in individual packaging (e.g. blister packs). In some embodiments, some or all of the individual doses of electrolytes are packed together in a multidose container (e.g. bottle, jar, bag, blister pack, envelope, etc.). In some embodiments, individual doses of electrolytes are grouped together in larger multi-doses doses. In some embodiments, the present invention provides an equal number of multi-doses doses of electrolytes and does of osmotic agent (e.g. 4 groups of electrolyte pills and 4 doses of osmotic agent). In some embodiments, doses of electrolytes are provided in a single unit with multiple compartments. In some embodiments, a specific number of doses of electrolytes are provided in a kit or package according to patient specific criteria (e.g. age, size, weight, sex, medical condition, species, etc.). In some embodiments, the number of electrolyte doses are prepared and/or assembled by a pharmacist based on clinician and/or manufacturer instructions. In some embodiments, the number of osmotic agent doses are preassembled into kits and/or packages, and a proper kit or package is selected for a subject based on subject specific criteria (e.g. age, size, weight, sex, medical condition, species, etc.).

In some embodiments, packages and/or kits of the present invention are provided with flavored drink mix to make the osmotic agent solution more palatable and/or drinkable. In some embodiments, doses of flavored drink mix are premeasured. In some embodiments, doses of flavored drink mix are provided in doses to be dissolved in a specified volume of clear liquid (e.g. 250 ml . . . 500 ml . . . 1000 ml . . . 1500 ml . . . 7000 ml, etc.). In some embodiments, does of flavored drink mix are provided in individual bags, blister packs, cups, bottles, jars, envelopes, and/or containers, etc. In some embodiments, packages and/or kits of the present invention are provided with one or more different flavors of flavored drink mix (e.g. banana, cherry, strawberry, watermelon, root beer, passion fruit, berry, etc.). In some embodiments, flavored drink mix is not provided with kits and/or packages of the present invention. In some embodiments, flavored drink mix to be used with the present invention must be provided by the patient or subject. In some embodiments, flavored drink mix is provided pre-dissolved in the appropriate volume of clear liquid (e.g. in dose-sized bottles). In some embodiments, an appropriate number of flavored drink mix doses are provided to correspond to the number of osmotic agent doses.

In some embodiments, compositions, kits, and or systems of the present invention may be packaged in any suitable manner. In some embodiments, all components are packaged in a single container (e.g. box, bag, vessel, bottle, envelope, etc.). In some embodiments, components are packaged in multiple containers. In some embodiments instructions are provided with kits/packaging of the present invention. The instructions may include a CD-ROM or DVD (or other media source) providing a video set of detailed instructions in addition to minted instructions. This may also include a link to a web site providing additional information, answers to frequently asked questions, troubleshooting, and also technical support.

Typical Products to Illustrate the Use of the Invention:

The following illustrate the use of two different prototypes that arise from the patent. They differ by the amount of polyethylene glycol (PEG) ingested and also by the composition and number of salt capsules. The working names for the products are PEG and Hi-PEG. Lo-PEG is essentially indistinguishable from water in taste and consistency, but requires that more capsules be ingested. Hi-PEG has a mildly slippery, waxy aftertaste, but uses only half the number of salt capsules that Lo-PEG uses.

Contents of Lo-PEC kit:

8 Packets of PEG 3350, each containing 29.5 grams of PEG 3350

44 capsules, each containing:

Sodium sulfate, 0.517 grams per capsule

Sodium bicarbonate, 0.153 grams per capsule

Sodium chloride, 0,133 grams per capsule

Potassium chloride, 0.067 grams per capsule

In some embodiments, one kit will have 8 blister packs, each blister pack containing a packet of PEG and 5 or 6 capsules, enough to use with one 500 ml bottle of water. The kit would also have a 500-600 ml cup for mixing, and also a product DVD/CD-ROM that goes over the prep in detail and also has a FAQ (frequently asked questions) section if 30 people are having trouble using the kit, Step One:

Ingest a low residue diet (basically, no fruits, nuts, or vegetables) beginning 3 to 5 days prior to procedure (this is common to most GI practices, for all preps).

Step Two:

Ingest a low residue breakfast the morning of prep day (again, this is standard for almost all preps).

Step Three:

ingest a clear liquid lunch ices, jello, tea, coffee) mid-day on the prep day.

Step Four:
Begin at 3 PM to 4 PM to Ingest the Kit as Follows:
Dissolve one 29.5 gram packet of PEG in 500 ml water
You may add Crystal light if you desire
Drink 500 ml of solution over 30 to 60 minutes
Consume 5 or 6 capsules during the 30 to 60 minutes that you consume the solution. One capsule every 5 to 10 minutes seems to be adequate.
Repeat Step four as above until you have ingested all 8 packets of PEG and all 44 capsules over the next 4 to 8 hours.
You may slow the rate of consumption if you feel bloated. Bloating tends to go away once you start passing stool.

This kit may be administered in a split dose format as well, with one-half to three-quarters of the kit being consumed on the day prior to the procedure, and the remaining one-half to one-quarter of the kit being consumed in the following morning, the day of the procedure.

The Second Product, Hi-PEG, is Used as Follows and is Quite Similar in its Use:
Contents of Hi-PEG kit (differences from Lo-PEG are in bold):
8 Packets of PEG 3350, each containing 52.5 grams of PEG 3350
capsules, each containing:
Sodium bicarbonate, 0.286 grams per capsule
Sodium chloride, 0.56 grams per capsule
Potassium chloride, 0,074 grams per capsule
(note that no sodium sulfate is used in the Hi-PEG formulation)

Step One:
Ingest a low residue diet (basically, no fruits, nuts, or vegetables) beginning 3 to 5 days prior to procedure (this is common to most GI practices, for all preps).

Step Two:
Ingest a low residue breakfast the morning of prep day.

Step Three:
Ingest a clear liquid lunch (juices, jello, tea, coffee) mid-day on the prep day.

Step Four:
Begin at 3 PM to 4 PM to Ingest the Kit as Follows:
Dissolve one 52.5 gram packet of PEG in 500 ml water
You may add Crystal light if you desire
Drink 500 ml of solution over 30 to 60 minutes
Consume 2 or 3 capsules during the 30 to 60 minutes that you consume the solution. One capsule every 10 to 20 minutes seems to be adequate.
Repeat Step four as above until you have ingested all 8 packets of PEG and all 20 capsules over the next 4 to 8 hours.
You may slow the rate of consumption if you feel bloated. Bloating tends to go away once you start passing stool. Some people stop drinking when they are bloated until they have a bowel movement, then resume drinking once the bloating is relieved. This practice is fine.

This kit may be administered in a split dose format as well, with one-half to three-quarters of the kit being consumed on the day prior to the procedure, and the remaining one-half to one-quarter of the kit being consumed in the following morning, the day of the procedure.

I claim:

1. A kit comprising:
a) one or a plurality of unit doses of an osmotic agent, formulated for administration to a patient after dissolving in water, wherein said plurality of individually packaged unit doses of an osmotic agent do not contain electrolytes; and separately;
b) one or a plurality of unit doses of a composition comprising electrolytes.

2. The kit of claim 1, further comprising a plurality of flavor packs.

3. The kit of claim 1, further comprising a plurality of containers wherein the one or a plurality of unit doses of osmotic agent are contained within at least one of said containers.

4. The kit of claim 3, where the containers additionally contain one or a plurality of units of flavor packs.

5. The kit of claim 3, wherein each container contains one unit dose of the osmotic agent and a flavoring agent.

6. The kit of claim 1, wherein the osmotic agent is PEG having average molecular weight between 2000 and 8000.

7. The kit of claim 1, wherein the osmotic agent is PEG 3350.

8. The kit of claim 1, wherein the electrolytes are independently selected from the group consisting of sodium sulfate, sodium bicarbonate, sodium chloride, potassium chloride, magnesium sulfate, magnesium citrate, ascorbic acid, and sodium ascorbate.

9. The kit of claim 1, wherein the electrolytes are independently selected from the group consisting of sodium bicarbonate, sodium chloride, and potassium chloride.

10. The kit of claim 8, wherein the electrolyte doses are in a pill, tablet, capsule, gel-cap, micro-encapsulated granules, or liquid form.

11. The kit of claim 9, wherein the electrolyte doses are in a pill, tablet, capsule gel-cap, micro-encapsulated granules, or liquid form.

12. The kit of claim 1, wherein the electrolyte dose comprises: from 0.2 g to 20 g sodium chloride; from 0.1 g to 5 g potassium chloride; and from 0.1 g to 10 g sodium bicarbonate.

13. The kit of claim 12, further comprising from 0.1 g to 40 g sodium sulfate.

14. The kit of claim 12, wherein the electrolyte doses are in a pill, tablet, gel-cap, micro-encapsulated granules, or capsule form and the electrolyte dose comprises from 0.5 g to 1 g sodium chloride; from 0.2 g to 0.5 g potassium chloride; from 0.7 g to 1 g sodium bicarbonate; and from 0.1 g to 4 g sodium sulfate.

15. The kit of claim 1, wherein the electrolyte dose comprises from 1 g to 2 g sodium chloride; from 0.1 g to 0.3 g KCl; and from 0.5 g to 1 g sodium bicarbonate.

16. The kit of claim 6, wherein the electrolyte doses are in a pill, tablet, capsule, gel-cap, micro-encapsulated granules, or liquid form and wherein a unit dose of PEG is from 20 g to 175 g of PEG 3350.

17. The kit of claim 16, wherein a unit dose of PEG is from 25 g to 100 g.

18. The kit of claim 16 wherein the unit dose of PEG is from 25 g to 35 g.

19. The kit of claim 16 wherein the unit dose of PEG from 50 g to 60 g.

20. A capsule, pill, gel-cap, micro-encapsulated granules, or a tablet which comprises sodium chloride, potassium chloride and sodium bicarbonate.

* * * * *